(12) United States Patent
Yeo

(10) Patent No.: US 8,620,421 B2
(45) Date of Patent: Dec. 31, 2013

(54) MASSAGE APPARATUS HAVING ION INJECTING FUNCTION

(75) Inventor: Myung Kwon Yeo, Bucheon (KR)

(73) Assignee: Toly Korea, Inc., Bucheon (KR)

( * ) Notice: Subject to any disclaimer, the term of this patent is extended or adjusted under 35 U.S.C. 154(b) by 0 days.

(21) Appl. No.: 12/758,883

(22) Filed: Apr. 13, 2010

(65) Prior Publication Data

US 2011/0251537 A1  Oct. 13, 2011

(51) Int. Cl.
*A61N 1/30* (2006.01)
(52) U.S. Cl.
USPC ............................................. 604/20
(58) Field of Classification Search
USPC ............................................. 604/20
See application file for complete search history.

(56) References Cited

U.S. PATENT DOCUMENTS

2010/0191171 A1* 7/2010 Park ............................ 604/20

* cited by examiner

*Primary Examiner* — Jason Flick
(74) *Attorney, Agent, or Firm* — Maxon IP LLC.; Justin H. Kim, Esq.

(57) ABSTRACT

A massaging apparatus capable of charging ion on a face contacting portion is provided.
The massaging apparatus capable of iontophoresis has an effect to make isometrics permeated deeply through skin by charging ion on the face contacting portion.
Further, the massaging apparatus capable of iontophoresis has another effect to prevent cosmetics from deterioration in advance by providing the airless pump container for blocking inflow of air.
Further, the massaging apparatus capable of iontophoresis has still another effect to increase credibility by including the self-awareness portion for making user aware whether ion is charged on the face contacting portion.

4 Claims, 3 Drawing Sheets

100

MASSAGE APPARATUS HAVING ION INJECTING FUNCTION

TECHNICAL FIELD

The present invention relates to a massaging apparatus capable of iontophoresis, more particularly relates to a massaging apparatus capable of charging ion on a face contacting portion so that cosmetics may permeate deeply through skin.

BACKGROUND ART

Generally, cosmetics is one of products for providing skin with nutrition or for eliminating body wastes in skin. After applying cosmetics on skin, user rubes it with hands or other equipment so that it may permeate deeply through skin.

But, it is not so easy that cosmetics permeates deeply into subcutaneous tissue through skin only by rubbing with hands or other equipments.

A steam towel is conventionally used to maximize pores, thereby permeation of cosmetics can be performed easily. But the steam towel helps only to expand width of path through which cosmetics moves. Thus, there is a limitation in elongating the depth of permeation.

DISCLOSURE

Technical Problem

An object of the present invention is to provide a massaging apparatus capable of iontophoresis which charges ion on a face contacting portion so that cosmetics may permeate deeply through skin.

Further, another object of the present invention is to provide a massaging apparatus capable of iontophoresis which has an airless pump therein, thereby inflow of air can be protected so that deterioration of cosmetics can be prevented.

Still another object of the present invention is to provide a massaging apparatus capable of iontophoresis which has a self-awareness portion to make user recognize whether ion is charged so that credibility can be increased.

Still another object of the present invention is to provide a massaging apparatus capable of iontophoresis which has a vibration motor so that cosmetics may permeate through skin more deeply when a face contacting portion is closed to face while user grips the massaging apparatus tightly.

Technical Solution

A massaging apparatus capable of iontophoresis according to the present invention includes: an airless pump container 10 for pumping contained cosmetics outward;

a rear case 20 where a settling portion 22 for settling the airless pump container 10, an aperture 24 on the top and an opening 28 for entrance of the airless pump 10 are provided;

a front case 30 engaged with the rear case 20 for providing inner space, where a forward-directed outlet 32 is provided on the top;

a button portion 40 for operating the airless pump container 10 provided on the aperture 24 of the rear case 20;

a face contacting portion 50 for contacting skin where an outlet 52 interconnected to an outlet 32 of the front case 30 is provided;

a supplying tube 56 for supplying content, which is discharged from the airless pump container 10, interposed between the face contacting portion 50 and the airless pump container 10;

a printed circuit board 60 inserted into the inner space resulted from the engagement of the front case 30 and the rear case 20;

a hand contacting portion 70 exposed from the inner space resulted from the engagement of the front case 30 and the rear case 20 for constructing a electrically closed circuit together with the face contacting portion 50, body of user and the printed circuit board 60 thereby acting as a switch;

an ion IC 90 for generating ion to be supplied to the face contacting portion 50 when the electrically closed circuit is constructed by the hand contacting portion 70, body of user, the face contacting portion 50 and the printed circuit board 60; and a power supply 80 for supplying power the printed circuit board 60.

It is preferable that the button portion 40 includes a cage 44 to which a head portion 14 of the airless pump container 10 is fixed, a pumping button 46 whose elevation is limited by a stopper 45 at the top of the cage 44 and a spring 49 interposed between the pumping button 46 and the top 29 of the settling portion 22 for supporting the pumping button 46 elastically.

It is further preferable to include self-awareness portion for generating a physical signal when the electrically closed circuit is constructed by the printed circuit board 60, the hand contacting portion 70, the face contacting portion 50 and body of user.

It is further preferable that the self-awareness portion is a vibration motor 92 or a display 94.

---Brief description of parts in drawings---

| | |
|---|---|
| 10: airless pump container | 20: rear case |
| 30: front case | 40: button portion |
| 50: face contacting portion | 60; printed circuit board |
| 70: hand contacting portion | 80: power supply |
| 90: ion IC | 100: massaging apparatus |

BEST MODE

Hereinafter, preferred embodiments of the present invention will be described in detail with reference to the accompanying drawings.

Figure 1:
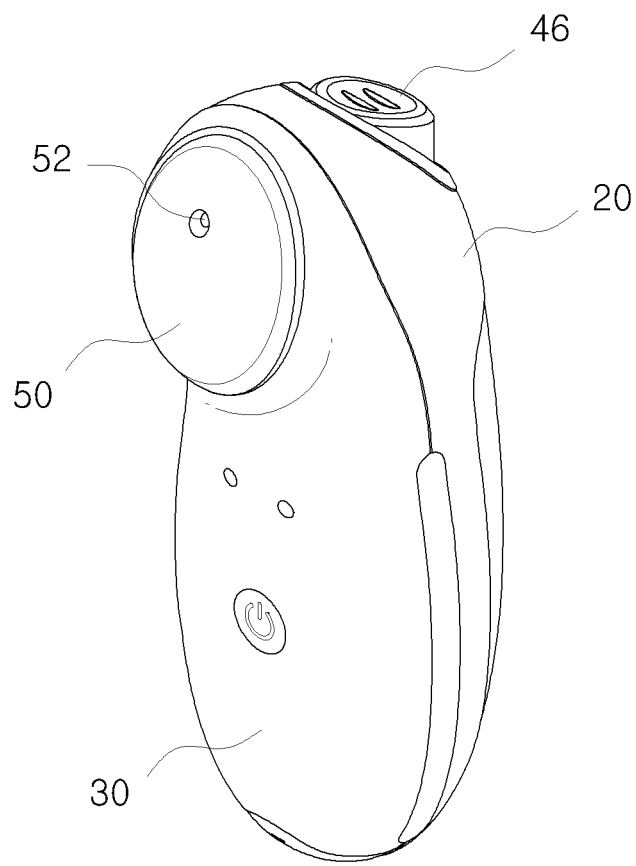
FIG. 1 shows a perspective view of the massaging apparatus capable of iontophoresis according to the present invention.
Figure 2:
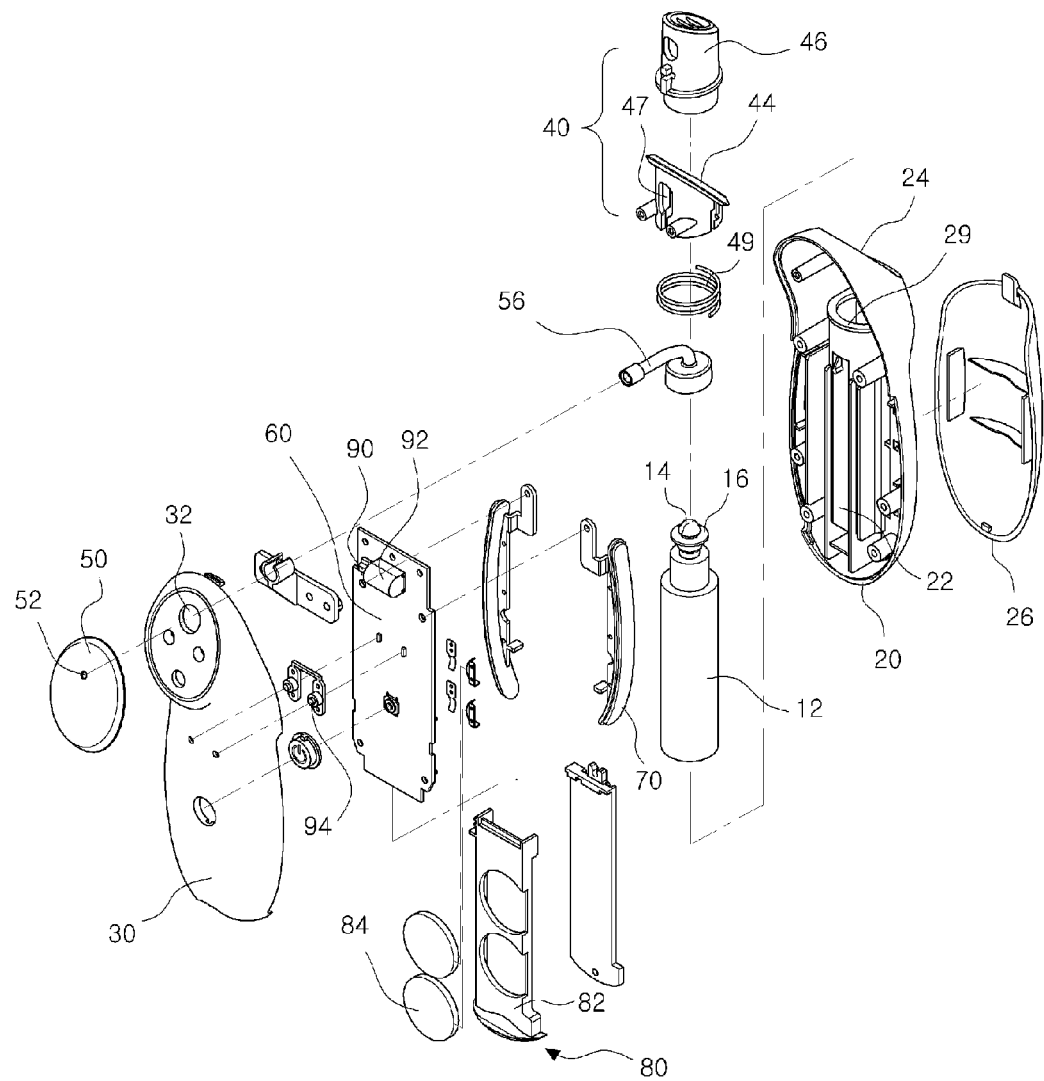
FIG. 2 shows disassembled perspective view of the massaging apparatus capable of iontophoresis according to the present invention.
Figure 3:
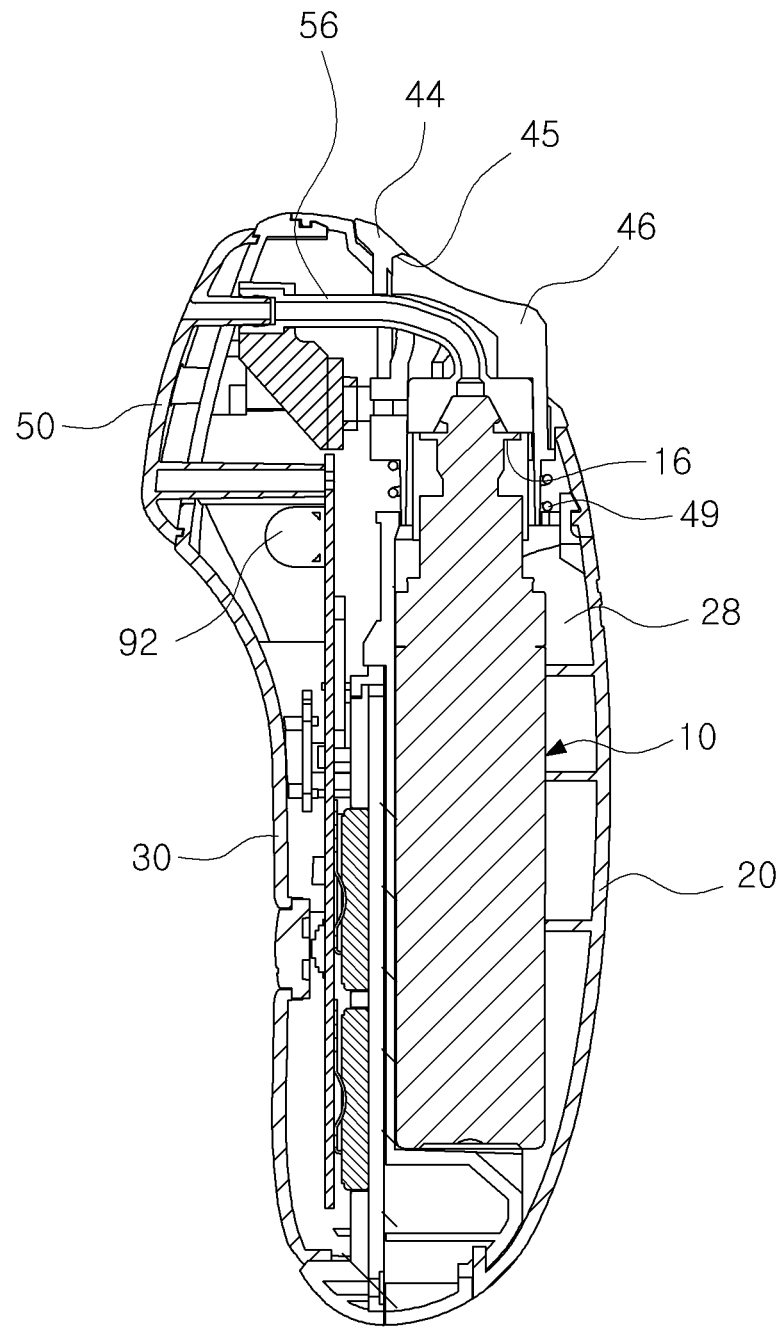
FIG. 3 shows a side sectional view of the massaging apparatus capable of iontophoresis according to the present invention.

The massaging apparatus capable of iontophoresis according to the present invention includes an airless pump container 10, a rear case 20 and a front case 30 for providing an inner space by engagement, a button portion 40 for operating the airless pump container 10, a face facing portion to contact to skin, a supplying tube 56 for supplying skin with content discharged from the airless pump container 10, a printed circuit board 60 which is inserted into the inner space provided by the engagement of the front case 30 and the rear case 20, a hand contacting portion 70 which is exposed outwardly from the inner space and functions as a switch, an ion IC 90 for supplying the face contacting portion 50 with ion and a power supply 50 for supplying the printed circuit board 60 with power, as shown FIG. 1 through FIG. 3.

The airless pump container 10 is an airless type container to which inflow of air is blocked. The airless pump container 10 pumps content contained therein out.

Because the airless pump container 10 is widely used in the field of cosmetics, medical supplies, etc, detailed description is omitted. Generally, the airless pump container 10 includes a body 12 for containing content and a head portion 14 on the top of the body 12 for pumping content out. In the embodiment of the present invention the head portion 14 has a circular flange 16 on its outer surface so that it can be hanged on the cage 42, which is described hereinafter.

A settling portion 22 for settling the airless pump container 10 is provided in the rear case 20. An aperture 24 for installing the button portion 40, which operates the airless pump 10, is provided on the top of the rear case 20.

An opening 28, through which the airless pump container 10 can be installed, is provided at the rear side of the rear case 20 and a detachable cover 26 is installed over the opening 28. A cylindrical portion for guiding the button portion 40 is provided in the aperture 24 at the top of the rear case 20.

The front case 30 is prepared to provide the inner space by the engagement with the rear case 20, a flat surface for installing the face contacting portion 50 is provided in the its front side and a outlet 32 for discharging content to the flat surface is provided thereto.

A button portion 40 for operating the airless pump container 10 is provided at the aperture 24 of the rear case 20. The button portion 40 includes a cage 44 which is provided at the head portion 14 of the airless pump container 10, a pumping button 46 provided at the top of the cage 44, and a spring 49 provided at the top 29 of the settling portion 22. Elevation of the pumping button 46 is limited by the stopper 45 at the top of the cage 44. A slot 47 is shaped at the side of the pumping button 46 in the perpendicular direction so that a supplying tube 56 can go through. The stopper 45 for limiting the elevation of the pumping button 46 is provided at the inner top of the cage 44. The pumping button 46 cannot be shaken because it is elastically supported at the top 29 of the settling portion 22 and the spring 49.

A face contacting portion 50 is provided on the flat surface of the front case 30 so that it can contact a user's skin. An outlet 52 is provided at the face of the contacting portion 50 so that cosmetics are discharged. The face contacting portion 50 is made of an electrical conductor so that it can be charged by ions generated from an ion IC 90.

The supplying tube 56 is provided between the airless pump container 10 and the outlet 52 of the face contacting portion 50 so that the content discharged from the airless pump container 10 can be supplied to the face contacting portion 50. The supplying tube 56 penetrates the outlet 32 of the front case 30. The supplying tube is made flexible because its location is variable according to the elevation of the airless pump container 10.

A printed circuit board 60 is placed in the inner space between the front case 30 and the rear case 20 and the ion IC 90 and a vibration motor 92 as a self-awareness portion are installed on the printed circuit board 60. The printed circuit board 60 is electrically connected to the face contacting portion 50, the hand contacting portion 70 and the body of user so that a electrically closed circuit can be constructed.

The hand contacting portion 70 is installed to be exposed outward from the inner space resulted by the engagement of the front case 30 and the rear case 20. and electrically connected to the face contacting portion 50, the skin of the user and the printed circuit board 60 so that an electrically closed circuit can be constructed. Accordingly, it is preferable that the hand contacting portion 70 functions as a switch when the user grabs it with her hands.

The ion IC 90 is an IC for generating galvanic ions and is provided on the printed circuit board 60. The ion IC 90 generates positive ions or negative ions as required, so that not only can cosmetics permeate deeply through the user's skin but also remaining body waste can be removed by changing polarity as necessary.

The Galvanic ion was discovered by a medical scientist Luigi Galvani who discovered the fact that electric current flows through the nerve in the body through the phenomenon that legs of craw was moved when spark discharge is occurred during the frog dissecting experiment. After that, iontophoresis for permeating ionic substance, which is difficult to permeate below the barrier zone under the horny layer, into the body through skin or the mucous membrane by using direct current (DC) is developed by scientists. Effectiveness of medicines or cosmetics can be increased because medicines or cosmetics can be permeated through watery hindrance layer of the cortico in the virtue of the iontophorisis.

The power supply 80 supplies the printed circuit board 60 with power and includes a battery 84 and a battery tray 82 for installing the battery 84. It is preferable that the battery is a button type to occupy small space.

The massaging apparatus capable of iontophoresis according to the embodiment of the present invention further includes a self-awareness portion for generating a physical phenomenon when ion is generated by the ion IC 90 that is, when a electrically closed circuit is constructed by the printed circuit board 60, the hand contacting portion 70, the face contacting portion 50 and body of user. Because the intensity of the ion charged on the face contacting portion 50 by the ion IC 90 is very small, user cannot aware whether ion is charged on the face contacting portion 50. For this reason, a self-awareness portion is provided to notify user whether ion is charged.

It is preferable that the self awareness portion is a vibration motor 92 for tactile sensation or a display 94 for visual sensation.

The massaging apparatus capable of iontophoresis according to the present invention has an effect to make cosmetics permeated deeply through skin by charging ion on the face contacting portion.

Further, the massaging apparatus capable of iontophoresis according to the present invention has another effect to prevent cosmetics from deterioration in advance by providing the airless pump container for blocking inflow of air.

Further, the massaging apparatus capable of iontophoresis according to the present invention has still another effect to increase credibility by including the self-awareness portion for making user aware whether ion is charged on the face contacting portion.

And further, the massaging apparatus capable of iontophoresis according to the present invention has still another effect to give user a good sense of contact by providing the vibration motor as a self aware portion.

The invention claimed is:

1. A massaging apparatus capable of iontopheresis, comprising:
an airless pump container containing a content;
a rear case and a front case defining an inner space by engagement;
a button portion for operating the airless pump container;
a face contacting portion defining a generally planar surface, the entire contacting portion establishing a planar contact with a portion of a user's skin during use, the contacting portion having an outlet inside the contacting portion, the contacting portion being made of an electrical conductor;

a supplying tube for supplying the contacting portion with content discharged from the airless pump container through the outlet;

a printed circuit board inserted into the inner space;

a hand contacting portion which is exposed outwardly from the inner space and functions as a switch;

an ion IC for generating ions on the face contacting portion so that the ions generated on the entire face contacting portion directly contact the user's skin while the content being discharged from the pump container is discharged to the face contacting portion; and a power supply for supplying the printed circuit board with power.

2. The massaging apparatus capable of iontophoresis of claim 1, wherein the button portion further comprises:

a cage to which a head portion of the airless pump container is fixed;

a pumping button whose elevation is limited by a stopper at the top of the cage; and a spring provided between the pumping button and a top of a setting portion for supporting the pumping button elastically.

3. The massaging apparatus capable of iontophoresis of claim 2, further comprising:

a self awareness portion for generating a physical signal when an electrically closed circuit is constructed by the printed circuit board, the hand contacting portion, the face contacting portion and the body of the user.

4. The massaging apparatus capable of iontophoresis of claim 3, wherein the self-awareness portion is a vibration motor or a display.

* * * * *